United States Patent
Dasbach et al.

(10) Patent No.: US 8,968,257 B2
(45) Date of Patent: Mar. 3, 2015

(54) CODED CARTRIDGE HOLDER SYSTEM FOR A FLUID DELIVERY DEVICE

(75) Inventors: Uwe Dasbach, Frankfurt am Main (DE); Steffen Raab, Frankfurt am Main (DE); Michael Harms, Frankfurt am Main (DE); Udo Stauder, Frankfurt am Main (DE); Volker Korger, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/642,554

(22) PCT Filed: Apr. 21, 2011

(86) PCT No.: PCT/EP2011/056472
§ 371 (c)(1),
(2), (4) Date: Feb. 5, 2013

(87) PCT Pub. No.: WO2011/131775
PCT Pub. Date: Oct. 27, 2011

(65) Prior Publication Data
US 2013/0211326 A1    Aug. 15, 2013

Related U.S. Application Data

(60) Provisional application No. 61/327,294, filed on Apr. 23, 2010.

(30) Foreign Application Priority Data

Jul. 22, 2010  (EP) .................................... 10170436

(51) Int. Cl.
  *A61M 5/315*  (2006.01)
  *A61M 5/50*   (2006.01)
  *A61M 5/24*   (2006.01)

(52) U.S. Cl.
  CPC ............... *A61M 5/5086* (2013.01); *A61M 5/24* (2013.01); *A61M 5/31551* (2013.01);
  (Continued)

(58) Field of Classification Search
  USPC ................. 604/232, 187, 186, 188, 192, 195, 604/207–218, 200, 201, 228, 233, 234
  See application file for complete search history.

(56) References Cited

U.S. PATENT DOCUMENTS

| | | | |
|---|---|---|---|
| 5,645,534 A * | 7/1997 | Chanoch | 604/189 |
| 6,210,369 B1 * | 4/2001 | Wilmot et al. | 604/157 |
| 7,175,055 B2 * | 2/2007 | Hansen et al. | 222/326 |
| 7,497,843 B1 | 3/2009 | Castillo et al. | |

(Continued)

FOREIGN PATENT DOCUMENTS

| | | |
|---|---|---|
| WO | 2008/062025 A1 | 5/2008 |
| WO | 2008/074897 A1 | 6/2008 |
| WO | 2010/006870 A1 | 1/2010 |

OTHER PUBLICATIONS

International Preliminary Report on Patentability for Int. App. No. PCT/EP2011/056472, mailed Nov. 1, 2012.

*Primary Examiner* — Scott Medway
(74) *Attorney, Agent, or Firm* — McDonnell Boehnen Hulbert & Berghoff LLP

(57) ABSTRACT

A coded cartridge holder system is disclosed for use with a cartridge assembly (20) containing a fluid and a delivery device (10), where the system has keyed connectors (5, 5', 6, 6') to prevent accidental attachment of the wrong fluid delivery device (10). The system comprises a coupling (1) attachable to the dose setting portion (12) of the device (10) and keyed to the proximal end of the cartridge holder (14). The cartridge holder (14) may also contain medical coding (27, 28) to correspond to matching coding (27', 28') on the distal end of a cartridge assembly (20).

20 Claims, 3 Drawing Sheets

(52) U.S. Cl.
CPC .................. *A61M 2005/2407* (2013.01); *A61M 2005/2433* (2013.01); *A61M 2005/2488* (2013.01); *A61M 2005/2492* (2013.01); *A61M 2205/6045* (2013.01)
USPC ........... 604/218; 604/232; 604/186; 604/187; 604/188; 604/192; 604/195; 604/207; 604/208; 604/209; 604/210; 604/211; 604/212; 604/213; 604/214; 604/215; 604/216; 604/217; 604/200; 604/201; 604/228; 604/233; 604/234

(56) References Cited

U.S. PATENT DOCUMENTS

| | | | |
|---|---|---|---|
| 8,568,364 B2 * | 10/2013 | Plumptre | 604/197 |
| 2006/0206057 A1 * | 9/2006 | DeRuntz et al. | 604/224 |
| 2008/0108951 A1 * | 5/2008 | Jerde et al. | 604/198 |
| 2013/0006192 A1 * | 1/2013 | Teucher et al. | 604/201 |
| 2013/0231614 A1 * | 9/2013 | Cross et al. | 604/198 |

* cited by examiner

CODED CARTRIDGE HOLDER SYSTEM FOR A FLUID DELIVERY DEVICE

This application is a U.S. national phase of International Application No. PCT/EP2011/056472 filed on Apr. 21, 2011, which claims priority to U.S. Provisional Application No. 61/327,294 filed on Apr. 23, 2010 and European Patent Application No. 10170436.9 filed Jul. 22, 2010, the disclosures of which are incorporated herein by reference in their entirety.

FIELD OF THE DISCLOSURE

Embodiments of the present disclosure relate to reservoir systems, particularly reservoirs containing a medicament. More particularly, the present disclosure is generally directed to a container or holder system for such reservoirs that contain one or more coding or keying features to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen-type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4. Insulin analogues are for example Gly(A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala (B26) human insulin; Des(B28-B30) human insulin; Des (B27) human insulin and Des(B30) human insulin. Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin. Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-S9)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

For example, with respect to insulin, a patient suffering from diabetes may require a certain amount of insulin to either be injected via a pen-type injection syringe or infused via a pump. With respect to certain known reusable pen-type drug delivery devices, a patient may load a cartridge containing the insulin into a proximal end of a cartridge holder. After the cartridge has been correctly loaded, the user may then be called upon to select a dose of the medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user may dispose of the empty cartridges properly. Where the drug delivery device comprises a disposable device, once the cartridge is empty, the user is recommended to dispose of the entire device.

Such known self-administration systems requiring the removal and reloading of empty cartridges have certain limitations. For example, in certain generally known systems, a user may simply load a new cartridge into the delivery system without the drug delivery device or without the cartridge having any mechanism of preventing cross use of an incorrect cartridge. That is, the drug delivery device does not have a mechanism for determining whether the medicament contained in the cartridge is indeed the correct type of medicament to be administered by the patient. Alternatively, certain known drug delivery devices do not present a mechanism for determining whether the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-acting insulin could result in injury or even death. This is especially true when a patient has two injection devices, one for short-acting insulin and one for long-acting insulin. It is very desirable to prevent the cartridge of short-acting insulin from accidentally being inserted into the long-acting injection device and vice versa.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g. 3 ml cartridges). Therefore, there may be a variety of cartridges supplied by a number of different suppliers and containing a different medicament but fitting a single drug delivery device. As just one example, a first cartridge containing a first medicament from a first supplier may fit a medical delivery device provided by a second supplier. As such, a user might be able to load an incorrect medicament into a drug delivery device and, then, dispense said medicament (such as a rapid or basal type of insulin) without being aware that the medical delivery device was perhaps neither designed nor intended to be used with such a cartridge.

As such, there is a growing desire from users, health care providers, caregivers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge and/or cartridge holder to its drug type and design an injection device that only accepts or works with the dedication or coded features provided on or with the cartridge and/or cartridge holder so as to prevent unwanted cartridge cross use. Similarly, there is also a general need for a dedicated cartridge that allows the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e. making it more difficult for counterfeiters to provide unregulated counterfeit medicament carrying products.

Problem to be Solved

A problem to be solved by the present disclosure is to provide a cartridge holder system and a fluid delivery device where the safety of the user is increased.

SUMMARY

One aspect relates to a coded cartridge holder system. The coded cartridge holder system may comprise a coupling. The coupling may have a proximal end. The coupling may have a distal end. The coupling may have an inner wall. The inner wall may define a bore. The bore may extend from the proximal end to the distal end. The proximal end of the coupling may be configured for releasable or permanent attachment to a dose setting portion of a fluid delivery device, e.g. a pen-type device such as a pen-type injector. The coupling may comprise at least one of, preferably a plurality of, keyed connectors. The keyed connectors may be provided on the inner wall, preferably on the distal end of the inner wall. The keyed connectors may be oriented along the main longitudinal axis of the coupling. In particular, the axial extent of the keyed connectors may be larger than the angular extent of the keyed connectors. The coded cartridge holder system may comprise a cartridge holder. The cartridge holder may have a proximal end. The cartridge holder, preferably the proximal end of the cartridge holder, may have at least one of, preferably a plurality of, corresponding keyed connectors. The corresponding keyed connectors may match the keyed connectors on the coupling. In particular, the keyed connectors on the coupling may be configured for attachment to the cartridge holder having the proximal end and containing the corresponding keyed connectors that match the keyed connectors on the coupling.

In one possible configuration, the keyed connectors on the coupling may comprise three, preferably equally spaced, slots. The keyed connectors on the coupling may comprise a fourth slot. The fourth slot may be offset from one of the three equally spaced slots by an angle $\alpha$. The corresponding keyed connectors can be, preferably radial, projections or other protrusions. The corresponding keyed connectors may be positioned around an outer bushing surface of the cartridge holder. In order for the cartridge holder to properly engage the coupling, there may be three, preferably radial, protrusions. The protrusions may be arranged on the proximal end of the cartridge holder. The three protrusions may also be equally spaced from one another. The cartridge holder may comprise a fourth projection. The fourth projection may be offset from one of the three equally spaced projections by an angle equal to $\alpha$. In this manner, the proximal end of the cartridge holder may act like a key that fits into a lock, i.e. the distal end of the coupling. Of course, the slots and protrusions could be reversed, i.e. the slots could be provided on the bushing surface of the cartridge holder and the protrusions on the coupling. Moreover, the engagement between the slots and protrusions could fit together in a similar fashion as a bayonet fitting, snap lock, twist fit, or combination of these types of couplings.

Preferably, the coupling is permanently attached to the dose setting portion of the injection device. Alternatively, the coupling could be removable or be integral to housing that comprises the distal end of the dose setting portion of the injection device. When configured for removal, the proximal end of the coupling preferably may have a connector that is configured for removable attachment to the dose setting portion of a fluid delivery device. The connector is most preferably a snap fit connector. The snap fit connector may be configured to engage a corresponding snap fit connector on the dose setting portion of the fluid delivery device. As soon as the coupling is connected to the dose setting portion of the device, the coupling may be secured against rotation with respect to the drug delivery device. At the distal end of the coupling there may be one or more releasable connectors, such as snap locks or bayonet fittings or a combination of both. It may be desirable to incorporate one more of these releasable connectors with the keyed connectors of the coupling and cartridge holder.

In another embodiment, there is a coded cartridge holder system as described above with the addition of a cartridge holder having a distal end and a proximal end that can accept a cartridge of fluid, preferably a medicament, for example insulin. The proximal end of the cartridge holder may have the corresponding keyed connectors that match the keyed connectors on the coupling. The distal end of the holder may have an interior wall. The interior wall may contain a mechanical coding. The mechanical coding may be configured for engagement with a cartridge assembly. In one embodiment, the mechanical coding may comprise three, preferably equally spaced, protrusions or slots. The mechanical coding may further comprise a fourth protrusion or slot offset from one of the three equally protrusions or slots by an angle $\beta$. In a most preferred system, there is a cartridge assembly. The cartridge assembly may have a distal end. The cartridge assembly, preferably the distal end of the cartridge assembly, may contain three, preferably equally spaced, radial slots or protrusions. The cartridge assembly, preferably the distal end of the cartridge assembly, may contain a fourth slot or protrusion. The forth slot or protrusion may be offset from one of the three equally spaced projections by an angle equal to $\beta$. The protrusions or slots on the cartridge assembly may be configured to match the mechanical coding on the interior wall of the cartridge holder.

The specific shape, size or form of the keyed connectors or mechanical coding is not critical to the present disclosure and, therefore, a number of shapes or designs may be used, provided that the coupling is keyed to the proximal end of the cartridge holder, and in those instances where a cartridge assembly is part of the system, the distal end of the cartridge assembly is coded to the inner wall of the distal end of the cartridge holder. The coupling and cartridge holder may be comprised of multiple bodies or segments, each having various materials of construction, depending on the need to have harder/stiffer parts. Preferred materials of construction of the coupling and of the associated cartridge holder include those selected from the group comprising plastics such as PP, acetal, polyamide, polyacetal (Delrin), acrylonitrile butadiene styrene (ABS), or, alternatively, metals, such as zinc, magnesium or aluminum, and mixtures of each of these materials as well.

A further aspect relates to a fluid delivery device. The fluid delivery device may be a pen-type device, in particular a pen-type injector. The fluid delivery device may comprise a dose setting portion. The fluid delivery device may comprise the previously described coded cartridge holder. A cartridge may be contained in the cartridge holder. The proximal end of the coupling may be permanently or releasably connected to the dose setting portion. The distal end of the coupling may be permanently or releasably connected to the cartridge holder.

According to a preferred embodiment, a coded cartridge holder system is provided which comprises a coupling having a proximal end, a distal end, and an inner wall defining a bore that extends from the proximal end to the distal end. The proximal end is configured for attachment to a dose setting portion of a fluid delivery device. The distal end of the inner wall has plurality of keyed connectors. The coded cartridge holder system comprises a cartridge holder having a proximal end having corresponding keyed connectors that match the keyed connectors on the coupling.

According to a preferred embodiment, a coded cartridge holder system is provided comprising a coupling having a proximal end, a distal end, and an inner wall The inner wall comprises a plurality of keyed connectors and the proximal end is configured for attachment to a to a dose setting portion of a fluid delivery device. The coded cartridge holder system comprises a cartridge holder comprising corresponding keyed connectors which are adapted and arranged to match the keyed connectors provided on the coupling.

According to a preferred embodiment, a coded cartridge holder system is provided comprising a coupling having a proximal end, a distal end, and an inner wall defining a bore that extends from the proximal end to the distal end. The proximal end is configured for attachment to a dose setting portion of a fluid delivery device. The distal end of the inner wall has plurality of keyed connectors. The coded cartridge holder system comprises cartridge holder having a distal end and a proximal end, where the proximal end has corresponding keyed connectors that match the keyed connectors on the coupling, and where the distal end has an interior wall comprising mechanical coding.

According to a preferred embodiment, a fluid delivery device is provided which comprises a dose setting portion and the previously described coded cartridge holder system. A cartridge is contained in the cartridge holder. The proximal end of the coupling is connected to the dose setting portion and the distal end of the coupling is connected to the cartridge holder.

These as well as other advantages of various aspects of the present disclosure will become apparent to those of ordinary skill in the art by reading the following detailed description, with appropriate reference to the accompanying figures.

The scope of the disclosure is defined by the content of the claims. The disclosure is not limited to specific embodiments but comprises any combination of elements of different embodiments. Moreover, the disclosure comprises any combination of claims and any combination of features disclosed by the claims.

BRIEF DESCRIPTION OF THE FIGURES

Exemplary embodiments are described herein with reference to the figures, in which.

DETAILED DESCRIPTION

Figure 1:
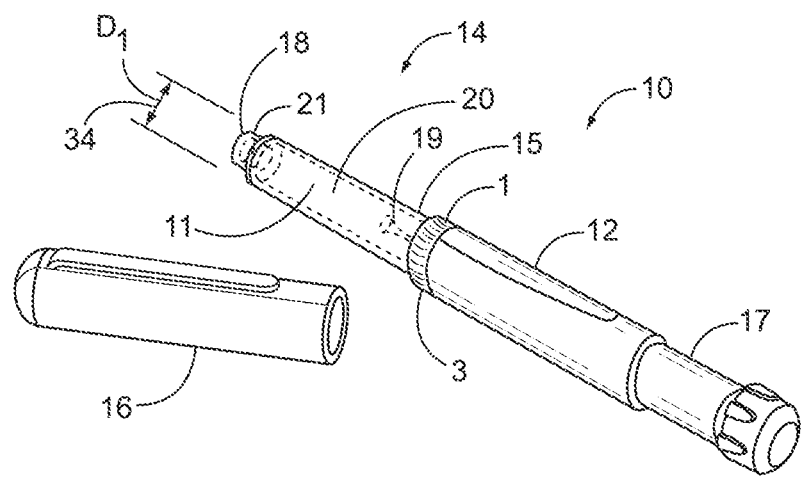
FIG. 1 illustrates an exemplary pen-type drug delivery device.

Referring to FIG. 1, there is shown a drug delivery device 10 in the form of a pen-type syringe. This drug delivery device 10 comprises a dose setting mechanism 12, a cartridge holder 14 and coupling 1, and a removable cap 16. A proximal end 15 of the cartridge holder 14 and a distal end 3 of the coupling 1 attached to dose setting mechanism 12 are removably secured together. The pen-type syringe may comprise a re-usable or a disposable pen-type syringe. Where the syringe comprises a re-usable device, the cartridge holder 14 and the dose setting mechanism are removably coupled together. In a disposable device, they are permanently coupled together. In FIG. 1, the dose setting mechanism 12 comprises a piston rod 19, such as a threaded piston rod that rotates when a dose is injected.

To inject a previously set dose, a double-ended needle assembly (not shown) is attached to a distal end 18 of the cartridge holder 14. Preferably, the distal end 18 of the holder 14 comprises a thread 21 (or other suitable connecting mechanism such as a snap lock, snap fit, form fit, or bayonet lock mechanism) so that the needle assembly may be removably attached to the distal end 18 of the holder 14. When the drug delivery device 10 is not in use, the removable cap 16 can be releasably retained over the cartridge holder 14.

Figure 2:
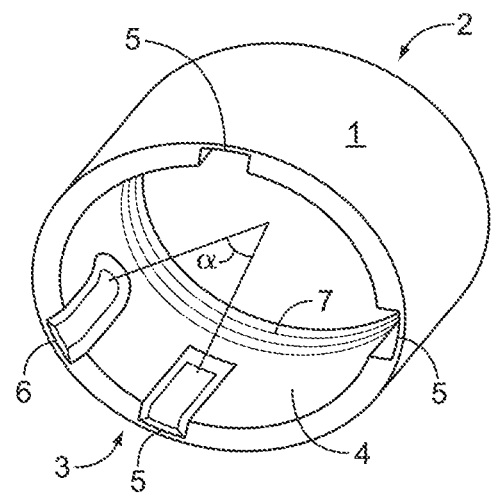
FIG. 2 illustrates a perspective view of one embodiment of the coupling that may be connected to the pen-type drug delivery device illustrated in FIG. 1.

FIG. 2 illustrates one example of the coupling 1. Coupling 1 has a distal end 3 and a proximal end 2 and is tubular in shape having an inner surface or inner wall 4. At the proximal end 2 of the inner surface 4 there is a connection means 7 for attachment to the dose setting mechanism 12, shown as threads 7. Once the coupling 1 is attached to the dose setting mechanism 12, rotation of the coupling 1 with respect to the dose setting mechanism 12 is prevented. As mentioned, preferably the attachment to the dose setting mechanism 12 is permanent or alternatively, the coupling 1 is integral to the distal portion of the housing of the dose setting mechanism 12. Although coupling 1 may be permanent attached to the dose setting portion of the injection device 10, it is configured to fit with different cartridge assemblies of the same type. The distal end 3 of the inner surface 4 of coupling 1 has a first group of keyed connectors 5 and at least one offset keyed connector 6. The first group of keyed connectors 5 are equally spaced around the inner circumference of coupling 1. These keyed connectors 5 are illustrated as slots or indentations on the inner surface 4, however, a variety of shapes and forms could be used. Offset keyed connector 6 is spaced an angle α from any one of the equally spaced keyed connectors 5. The angle α may be any angle between 0° and 180°, for example. Preferably, the angle α amounts to 45°. The keyed connectors 5, 6 are oriented along the main longitudinal axis of the coupling 1. In particular, the axial extent of the keyed connectors 5, 6 is larger than their angular extent.

Figure 3:
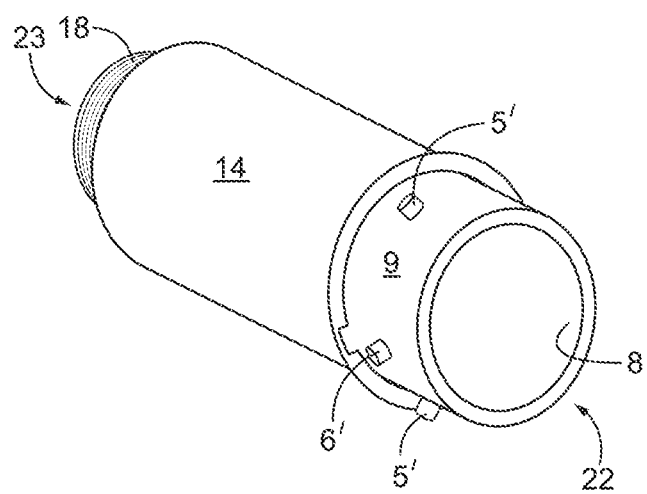
FIG. 3 illustrates a perspective view of a cartridge holder with one embodiment of the keyed connector for engagement with the coupling shown in FIG. 2.

Coupling 1 is configured to form a keyed, removable attachment to the cartridge holder 14. Cartridge holder 14 has a distal end 23 and a proximal end 22, as shown in FIG. 3. At the proximal end 22, there is a bushing surface 9 that contains a set of keyed connectors 5' and 6' that correspond to keyed connectors 5 and 6 on coupling 1. To allow the cartridge holder 14 to connect to coupling 1, connector 6' must be offset from one of the equally spaced connectors 5' an angle equal to α. One or more of the keyed connectors 5', 6' can include a snap fit or bayonet lock feature to allow the cartridge holder 14 to be securely attached to the coupling 1. Preferably, the shape and size of the keyed connectors 5' and 6' are configured to achieve a "glove-in-hand" fit or secure connection with corresponding keyed connectors 5 and 6.

Figure 4:
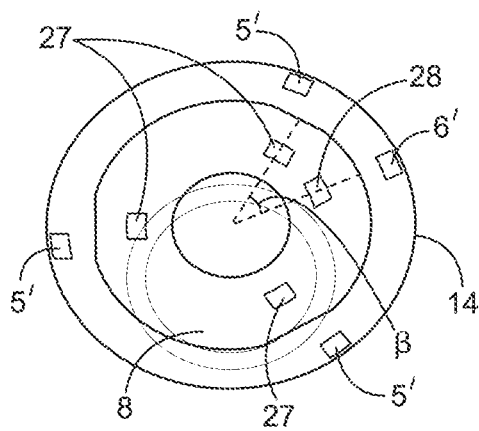
FIG. 4 illustrates an end view of the distal end of the inside of a cartridge holder showing one embodiment of the mechanical coding.
Figure 5:
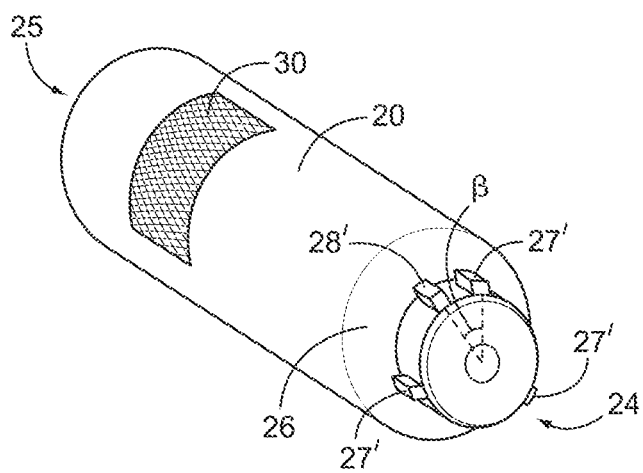
FIG. 5 illustrates one embodiment of the distal end of a cartridge assembly that has mechanical coding that corresponds to the coding shown in FIG. 4.

Cartridge holder 14 has an inner wall 8 defining a cavity that is dimensioned and configured to securely receive and retain a cartridge assembly 20 (see FIG. 5). In one preferred embodiment, at the distal end 23 of the cavity, as illustrated in FIG. 4, is a mechanical coding that is similar to the keyed connectors 5, 6 and 5', 6' on coupling 1 and the bushing surface 9. The mechanical coding comprises three equally spaced slots 27 and an offset slot 28. Offset slot 28 is positioned an angle β from one of slots 27. The angle β may be any angle between 0° and 180°, for example. Preferably, the angle β amounts to 45°.

Figure 6:
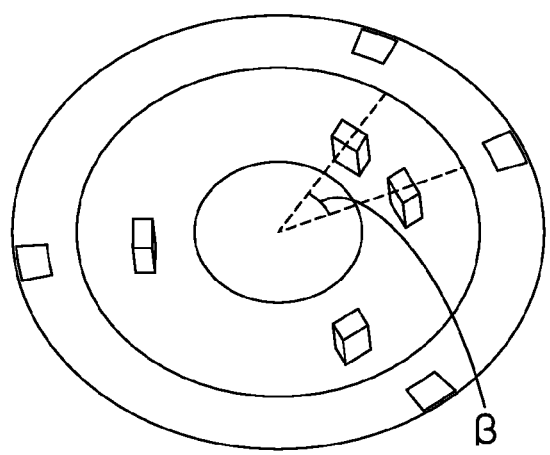
FIG. 6 illustrates an end view of the distal end of the inside of a cartridge holder showing one embodiment of the mechanical coding.
Figure 7:
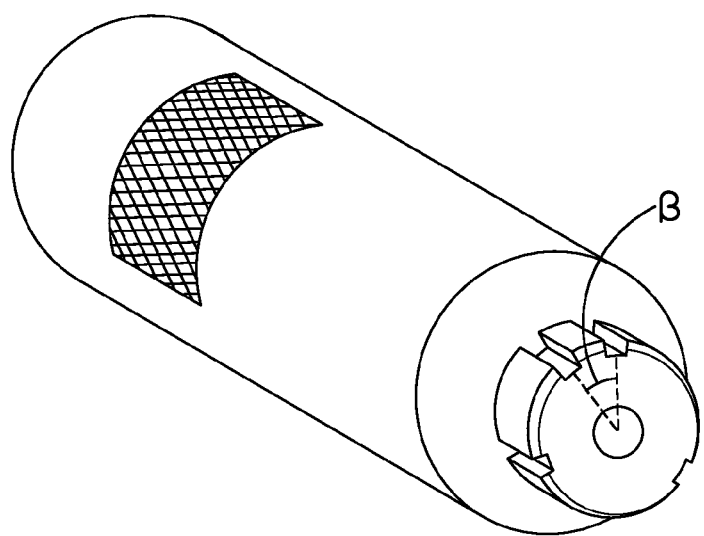
FIG. 7 illustrates one embodiment of the distal end of a cartridge assembly that has mechanical coding that corresponds to the coding shown in FIG. 6.

The corresponding cartridge assembly 20 (see FIG. 5) is configured to fit within cartridge holder 14. Typically, the assembly 20 comprises a hollow cartridge having a movable bung 30 or piston sealing the proximal end of the cartridge. The cartridge is usually manufactured of glass and includes a generally tubular barrel extending from a distal end 24 to a proximal end 25 and having a neck portion 26 (see FIG. 5), which is of a smaller diameter than the tubular barrel. The neck 26 preferably has a mechanical coding portion that corresponds to the coding found in the distal end of the cavity of the cartridge holder 14. One preferred embodiment would include radial protrusions 27' and 28' that correspond to slots 27 and 28 on the inside distal end of cartridge holder 14 (see FIG. 4). The coding on the distal end of cartridge assembly 20 can be made of any known materials that will form a tight fit to the outer wall of the neck portion 26 of the cartridge. Acceptable materials include metals that can be crimped or shrunk fit around a circumferential bead at the distal end of the neck 26. Of course, as with the coupling, the slots/protrusions on the cartridge assembly 20 and cartridge holder 14 can be reversed from that shown in FIGS. 4-5. For instance, FIG. 6 depicts a distal end of a cartridge holder comprising an interior wall comprising a mechanical coding, wherein the mechanical coding comprises three equally spaced protrusions and a fourth protrusion offset an angle β from one of the three equally spaced protrusions. Further, FIG. 7 depicts a cartridge comprising a distal end, wherein the distal end comprises three equally space radial slots and a fourth slot offset from one of the three equally spaced slots by an angle equal to β, the slots being configured to match the mechanical coding provided on the interior wall of the cartridge holder.

Axially directed forces acting upon the stopper/bung 30 within the cartridge during dose injection or dose administration urges the fluid from the cartridge through a dispensing interface, such as a double ended needle, mounted onto the distal end 18 of the cartridge holder 14. Such axially forces may be provided by the piston rod 19 working in unison with dose setting member 12.

A portion of the cartridge holder 14 defining the cartridge holder cavity is of substantially uniform diameter represented in FIG. 1 by D1 34. This diameter is preferably slightly greater than the diameter of the cartridge assembly 20. The interior of the cartridge holder 14 can include an inwardly-extending annular portion or stop that is dimensioned to prevent the cartridge assembly 20 from moving within the cartridge holder 14. In this manner, when the cartridge assembly 20 is loaded into the cavity of the cartridge holder 14 and the cartridge holder 14 is then connected to the dose setting member 12, the cartridge assembly 20 will be securely held within the cartridge cavity.

A number of doses of a medicament may be dispensed from the cartridge assembly 20. Preferably, the cartridge assembly 20 contains a type of medicament that must be administered often, such as one or more times a day. One such medicament is insulin.

The dose setting mechanism 12 comprises a dose setter 17 at the proximal end of the dose setting mechanism 12. In one preferred arrangement, the dose setter 17 is rotated to set a dose. To administer this set dose, the user may attach a needle assembly comprising a double ended needle on the distal end of the cartridge holder 14. In this manner, the needle assembly pierces a seal/septum at the distal end of the cartridge assembly 20 and is, therefore, in liquid communication with the medicament. The user pushes on the dose setter 17 to inject the set dose. The same dose setting and dose administration procedure is followed until the medicament in the cartridge assembly 20 is expended and then a new cartridge assembly must be loaded in the device. To exchange an empty cartridge assembly 20, the user is called upon to remove the cartridge holder 14 from the dose setting mechanism 12.

Employing the keyed connectors 5, 5', 6, 6' and optionally the mechanical coding 27, 28 inside the cartridge holder 14 offers a number of advantages. For example, by incorporating the keyed connectors 5, 5', 6, 6' in the coupling 1 and proximal end of the cartridge holder 14 may enable a more robust and finer coding scheme than could be applied by using a coding system only on the proximal end of the cartridge assembly 20.

One advantage of utilizing keyed connectors 5, 5', 6, 6' between the coupling 1 and the cartridge holder 14, and between the cartridge holder 14 and the cartridge assembly 20 is that such a coding scheme prevents a standard cartridge assembly 20 from being used with the coded cartridge holder 14 and, likewise, a standard cartridge holder with a coded coupling attached to a fluid delivery device. For example, if a user tried to insert a non-coded cartridge holder into the coded coupling 1, the user would be unable to make a connection. Consequently, thereby assembly of the cartridge holder 14 to the dose setting member 12 of the device 10 may be prevented.

Another advantage of having the mechanical coding between the cartridge assembly 20 and the cartridge holder 14 is that it prevents rotation of the cartridge assembly 20 when a double ended needle is mounted onto the distal end of the cartridge holder 14 which may occur by threading the needle assembly onto a receiving thread at the distal end of the cartridge holder 14.

Although aimed primarily at the insulin market, the present disclosure may apply to other drugs. The present disclosure may apply to various devices, including the following examples:

An injector pen with a cartridge (e.g. 3 ml cylindrical glass cartridge) and a separate holder. An injector pen with a cartridge (e.g. 3 ml cylindrical glass cartridge) non-removably retained in a holder, so that the holder will be disposed of with the primary pack. An injector pen where the primary pack attaches directly to the pen, e.g. an injection-molded polymer cartridge. Any drug delivery device with any type of reservoir or primary pack, e.g. inhaler, pouch.

The present disclosure with its coding features results in a number of advantages. For example, the proposed coded parts assist a user to distinguish between medicaments, thereby helping to ensure that a delivery device can only be used with a medicament for which the device is intended. Therefore, with the system applied to a cartridge, the cartridge is prevented from being confused with any other drug by loading a cartridge with an incorrect or unwanted interface.

The coded parts also result in a low cost coding mechanism since the proposed keying inserts do not require a large number of parts and can be manufactured in a cost effective manner. Moreover, there are quite a large number of different coding configurations between the parts that may be used. Consequently, with the proposed coding schemes, a large number of medicaments can be distinguished from one another. In addition, if a user attempts to load an incorrect cartridge into a cartridge holder designed for a different cartridge, the user will be alerted at an early stage of the assembly process.

In addition, the present disclosure can be used to prevent errors during manufacturing, when inserting the cartridge into disposable cartridge holders or disposable devices. Because the materials of construction of the main body and the second body are drug compatible and the coding features are on these bodies, there is no risk of drug contact with incompatible materials. Since the mechanical coding is fixed to the inside of the cartridge, the coded features cannot be removed without destroying the cartridge assembly, thus making the design relatively tamper proof.

Exemplary embodiments of the present disclosure have been described. However, as those of skill in the art will recognize certain changes or modifications to such arrangements may be made. As just one example, certain coding elements of one of the preferred arrangements discussed herein may be taken from one arrangement and combined with certain coding arrangements of other arrangements.

Those skilled in the art will understand, however, that further changes, modifications, revisions and/or additions may be made to the presently disclosed arrangements without departing from the true scope and spirit of the present disclosure, which is defined by the claims.

REFERENCE NUMERALS 1 coupling
2 proximal end
3 distal end
4 inner surface
5 keyed connector
5' keyed connector
6 keyed connector
6' keyed connector
7 thread
8 inner wall
9 bushing surface
10 drug delivery device
12 dose setting mechanism/dose setting member
14 cartridge holder
15 proximal end
16 removable cap
17 dose setter
18 distal end
19 piston rod
20 cartridge assembly
21 thread
22 proximal end
23 distal end
24 distal end
25 proximal end
26 neck portion
27 slot
27' radial protrusion
28 slot
28' radial protrusion
30 movable bung/stopper
34 D1

The invention claimed is:

1. A coded cartridge holder system comprising:
a coupling having a proximal end, a distal end, and an inner wall, the inner wall comprising a plurality of keyed connectors and the proximal end being configured for attachment to a dose setting portion of a fluid delivery device,
a cartridge holder comprising corresponding keyed connectors which are adapted and arranged to match the keyed connectors provided on the coupling, wherein the cartridge holder comprises a distal end, the distal end comprising an interior wall comprising a mechanical coding, wherein the mechanical coding comprises three equally spaced slots and a fourth slot offset an angle β from one of the three equally spaced slots, and
a cartridge comprising a distal end, wherein the distal end comprises three equally space protrusions and a fourth protrusion offset from one of the three equally spaced protrusions by an angle equal to β, the protrusions being configured to match the mechanical coding provided on the interior wall of the cartridge holder.

2. The coded cartridge holder system according to claim 1, wherein the inner wall is configured to define a bore that extends from the proximal end to the distal end.

3. The coded cartridge holder system according to claim 1, wherein the keyed connectors of the coupling are provided on the distal end of the inner wall.

4. The coded cartridge holder system according to claim 1, wherein the cartridge holder comprises a proximal end, the corresponding keyed connectors being provided on the proximal end of the cartridge holder.

5. The coded cartridge holder system according to claim 1, wherein the keyed connectors of the coupling comprise three equally spaced slots and a fourth slot offset an angle α from one of the three equally spaced slots.

6. The coded cartridge holder system according to claim 1, wherein the corresponding keyed connectors comprise radial projections positioned around an outer bushing surface of the cartridge holder.

7. The coded cartridge holder system according to claim 5, wherein the corresponding keyed connectors comprise three equally spaced radial projections and a fourth projection offset an angle equal to α from one of the three equally spaced projections.

8. The coded cartridge holder system according to claim 1, wherein the proximal end is configured for removable attachment to the dose setting portion of the fluid delivery device.

9. A fluid delivery device comprising a dose setting portion and the coded cartridge holder system according to claim 1, wherein a cartridge is contained in the cartridge holder, and wherein the proximal end of the coupling is connected to the dose setting portion and the distal end of the coupling is connected to the cartridge holder.

10. A coded cartridge holder system comprising:
a coupling having a proximal end, a distal end, and an inner wall, the inner wall comprising a plurality of keyed connectors and the proximal end being configured for attachment to a dose setting portion of a fluid delivery device;
a cartridge holder comprising corresponding keyed connectors which are adapted and arranged to match the keyed connectors provided on the coupling, wherein the cartridge holder comprises a distal end, the distal end comprising an interior wall comprising a mechanical coding, wherein the mechanical coding comprises three equally spaced slots and a fourth slot offset an angle β from one of the three equally spaced slots; and a cartridge comprising a distal end, wherein the distal end comprises three equally space protrusions and a fourth protrusion offset from one of the three equally spaced protrusions by an angle equal to β, the protrusions being configured to match the mechanical coding provided on the interior wall of the cartridge holder.

11. The coded cartridge holder system according to claim 10,
wherein the inner wall is configured to define a bore that extends from the proximal end to the distal end.

12. The coded cartridge holder system according to claim 10,
wherein the keyed connectors of the coupling are provided on the distal end of the inner wall.

13. The coded cartridge holder system according to claim 10,
wherein the cartridge holder comprises a proximal end, the corresponding keyed connectors being provided on the proximal end of the cartridge holder.

14. The coded cartridge holder system according to claim 10,
wherein the keyed connectors of the coupling comprise three equally spaced slots and a fourth slot offset an angle α from one of the three equally spaced slots.

15. The coded cartridge holder system according to claim 10,
wherein the corresponding keyed connectors comprise radial projections positioned around an outer bushing surface of the cartridge holder.

16. The coded cartridge holder system according to claim 14,
wherein the corresponding keyed connectors comprise three equally spaced radial projections and a fourth projection offset an angle equal to α from one of the three equally spaced projections.

17. The coded cartridge holder system according to claim 10,
wherein the proximal end is configured for removable attachment to the dose setting portion of the fluid delivery device.

18. The coded cartridge holder system according to claim 10,
wherein the coupling comprises a snap fit connector that is configured to engage a corresponding snap fit connector on the dose setting portion of the fluid delivery device.

19. The coded cartridge holder system according to claim 18, wherein the proximal end of the coupling comprises the snap fit connector.

20. A fluid delivery device comprising a dose setting portion and the coded cartridge holder system according to claim 10, wherein a cartridge is contained in the cartridge holder, and wherein the proximal end of the coupling is connected to the dose setting portion and the distal end of the coupling is connected to the cartridge holder.

* * * * *